(12) United States Patent
DiCesare et al.

(10) Patent No.: US 6,516,953 B1
(45) Date of Patent: Feb. 11, 2003

(54) DEVICE FOR SEPARATING COMPONENTS OF A FLUID SAMPLE

(75) Inventors: Paul C. DiCesare, Norwalk, CT (US); Jeffrey Karg, Hopkinton, MA (US); Fu-Chung Lin, Wayne, NJ (US); Jeffrey P. Radziunas, Wallingford, CT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 09/452,981

(22) Filed: Dec. 2, 1999

Related U.S. Application Data (60) Provisional application No. 60/110,927, filed on Dec. 5, 1998.

(51) Int. Cl.$^7$ ............................................... B01D 21/26
(52) U.S. Cl. ..................... 210/516; 210/513; 210/518
(58) Field of Search ................................. 210/782, 789, 210/513, 516, 518

(56) References Cited

U.S. PATENT DOCUMENTS

| | | | |
|---|---|---|---|
| 3,779,383 A | 12/1973 | Ayres | 210/516 |
| 3,849,072 A | 11/1974 | Ayres | |
| 3,897,343 A | 7/1975 | Ayers | 210/516 |
| 4,083,788 A | 4/1978 | Ferrara | |
| 4,088,582 A | 5/1978 | Murty et al. | |
| 4,131,549 A | 12/1978 | Ferrara | |
| 4,154,690 A | 5/1979 | Ballies | |
| 4,257,886 A | 3/1981 | Kessler | |
| 4,364,832 A | 12/1982 | Ballies | |
| 4,417,981 A | 11/1983 | Nugent | |
| 4,426,290 A | 1/1984 | Ichikawa et al. | 210/516 |
| 4,443,345 A | 4/1984 | Wells | |
| 4,818,386 A | 4/1989 | Burns | |
| 4,853,137 A | 8/1989 | Ersson | |
| 4,877,520 A | 10/1989 | Burns | |
| 5,269,927 A | 12/1993 | Fiehler | |
| 5,455,009 A | 10/1995 | Vogler et al. | |
| 5,575,778 A | * 11/1996 | Hardt et al. | 604/200 |
| 5,632,905 A | 5/1997 | Haynes | |
| 6,063,297 A | 5/2000 | Antanavich et al. | |

FOREIGN PATENT DOCUMENTS

| | | |
|---|---|---|
| EP | 0 017 127 | 3/1980 |
| EP | 0 627 261 A2 | 6/1994 |
| EP | 0 638 804 A1 | 8/1994 |
| EP | 0 638 804 A1 | 2/1995 |
| JP | 6-222055 | 8/1994 |
| WO | WO 98/51411 | 11/1998 |

* cited by examiner

*Primary Examiner*—John Kim
(74) *Attorney, Agent, or Firm*—Nanette S. Thomas, Esq.; Scott J. Rittman, Esq.

(57) ABSTRACT

A device and method is provided for separating components of a fluid sample. The device includes a plurality of constituents comprising a container, a liner in the container, a closure for the container and a composite element. The composite element is a seal plug with a density between the densities of the components of the fluid sample is releasably engaged with the container closure and with the liner. A needle cannula is used to deposit a fluid sample in the liner and the entire device is placed in a centrifuge. The centrifugal load causes the seal plug to separate from the closure and causes the liner to expand outwardly against the container. The seal plug migrates into the fluid sample and stabilizes between the densities of the components of the fluid sample. The liner will resiliently return to its initial configuration upon termination of centrifugal load such that the liner sealingly engages the seal plug and separates the components of the fluid sample.

9 Claims, 9 Drawing Sheets

DEVICE FOR SEPARATING COMPONENTS OF A FLUID SAMPLE

This application claims the benefit of Provisional Application No. 60/110,927, filed Dec. 5, 1998.

BACKGROUND OF THE INVENTION

1. Field of the Invention

This invention relates to a device and method for separating heavier and lighter fractions of a fluid sample. More particularly, this invention relates to a device and method for collecting and transporting fluid samples whereby the device and fluid sample are subjected to centrifugation to cause separation of the heavier fraction from the lighter fraction of the fluid sample.

2. Description of Related Art

Diagnostic tests may require separation of a patient's whole blood sample into components, such as serum or plasma, the lighter phase component, and red blood cells, the heavier phase component. Samples of whole blood are typically collected by venipuncture through a cannula or needle attached to a syringe or an evacuated collection tube. Separation of the blood into serum or plasma and red blood cells is then accomplished by rotation of the syringe or tube in a centrifuge. Such arrangements use a barrier for moving into an area adjacent the two phases of the sample being separated to maintain the components separated for subsequent examination of the individual components.

A variety of devices have been used in collection devices to divide the area between the heavier and lighter phases of a fluid sample.

The most widely used device includes thixotropic gel materials such as polyester gels in a tube. The present polyester gel serum separation tubes require special manufacturing equipment to prepare the gel and to fill the tubes. Moreover, the shelf-life of the product is limited in that overtime globules may be released from the gel mass. These globules have a specific gravity that is less than the separated serum and may float in the serum and may clog the measuring instruments, such as the instrument probes used during clinical examination of the sample collected in the tube. Such clogging can lead to considerable downtime for the instrument to remove the clog.

No commercially available gel is completely chemically inert to all analytes. If certain drugs are present in the blood sample when it is taken, there can be an adverse chemical reaction with the gel interface.

Therefore, a need exists for a separator device that (i) is easily used to separate a blood sample; (ii) is independent of temperature during storage and shipping; (iii) is stable to radiation sterilization; (iv) employs the benefits of a thixotropic gel barrier yet avoids the many disadvantages of placing a gel in contact with the separated blood components; (v) minimizes cross contamination of the heavier and lighter phases of the sample during centrifugation; (vi) minimizes adhesion of the lower and higher density materials against the separator device; (vii) can be used with standard sampling equipment; (viii) is able to move into position to form a barrier in less time than conventional methods and devices; and (ix) is able to provide a clearer specimen with less cell contamination than conventional methods and devices.

SUMMARY OF THE INVENTION

The present invention is a method and assembly for separating a fluid sample into a higher specific gravity phase and a lower specific gravity phase. Desirably, the assembly of the present invention comprises a plurality of constituents. Preferably, the assembly comprises a container, a liner and a composite element.

The container may be a conventional tube having a closed bottom, an opened top and a rigid cylindrical wall extending therebetween. The tube may include an inwardly directed rim near the open top.

The assembly further comprises a liner having a closed bottom, an open top and a tubular side wall. The liner is positioned in the tube such that the closed bottom of the liner is near the closed bottom of the tube. The liner, in an unbiased condition, is cross-sectionally dimensioned along most of its length to lie in spaced relationship to the tube. However, the liner may include an outwardly directed flange substantially adjacent the top of the liner. The flange may be dimensioned for engagement against the rim of the tube to position the liner longitudinally within the tube.

Preferably, the liner comprises a qualitative stiffness that may be characterized by a non-dimensional stiffness coefficient, S* and expressed as follows:

$$S^* = \frac{E(OD - D)}{a\rho_w D^2}$$

where E is the modulus of elasticity, OD is the thickness defined by the outside diameter, D is the seal diameter, a is the applied acceleration, and $\rho_w$ is the density of water. The stiffness coefficient is about 0.003 to about 190.

Preferably, the liner has a thickness of about 1.0 mm to about 2.5 mm, a modulus of elasticity of about 13.8 MPa to about 69 MPa.

Preferably, the assembly of the present invention will function under load created by an applied acceleration of about 300 g to about 3000 g.

Preferably, the liner deforms due to hydrostatic pressure under applied acceleration and returns to its initial state upon removal of the acceleration, thereby forming a seal by constricting the seal plug which is positioned in a target density region between the higher density portion and the lower density portion of a fluid sample.

The assembly further includes a tube closure that is sealingly engageable in the open top of the tube. The tube closure may include a tube end seat having an outside diameter at least equal to the outside diameter of the tube for disposition substantially adjacent the open top of the tube. The tube closure may include a tube stopper dimensioned for sealed engagement in portions of the tube between the top of the tube and the top of the liner. The tube closure may further include a liner stopper dimensioned for sealing engagement in the open top of the liner.

A plug recess extends into the bottom end of the tube closure. The entry to the plug recess may have a plurality of inwardly extending circumferentially spaced flexible walls.

Preferably, the composite element comprises a seal plug. The seal plug may be a single constituent or a plurality of constituents and comprises a specific density at a target density range as defined by separable fluid components densities. The seal plug may migrate freely when under an applied acceleration to settle at a location in the fluid sample in the target density region and thereby become a barrier at a desired level between the components of the fluid sample after the acceleration is removed.

Preferably, the seal plug has an aggregate specific gravity of about 1.028 to about 1.09. Most preferably, the seal plug has an aggregate specific gravity so that it will rest after centrifugal force, between the heavier and lighter phases of a blood sample.

The seal plug preferably has an overall density between the densities of two phases of a blood sample. The seal plug comprises a hard plastic shell having opposed first and second ends and an aperture extending between the ends. Outer circumferential portions of the hard plastic shell in proximity to the first end are dimensioned and configured for releasable engagement within the plug recess of the tube closure. Outer circumferential portions of the hard plastic shell in proximity to the second end are dimensioned for sealing engagement by the unbiased tube liner. The seal plug further includes an elastomeric septum that is securely mounted around the first end of the hard plastic shell to provide a pierceable barrier extending across the central passage through the shell.

Preferably, the seal plug comprises an overall specific gravity at a target specific gravity of $\sigma_t$. The target specific gravity is that required to separate a fluid sample into two phases.

In use, a fluid sample enters the assembly by a needle. The needle penetrates the closure and through the elastomeric septum on the seal plug for delivering a fluid sample into the liner. The needle is withdrawn from the assembly and the assembly is subjected to centrifugation. Forces exerted by the centrifuge cause the seal plug to separate from the tube closure and cause the liner to expand outwardly against the tube. Centrifugal forces then cause the seal plug to move through the expanded liner and toward the closed bottom of the tube. Sufficient movement will cause the seal plug to contact the fluid. Air trapped in the passage through the hard plastic liner and between the fluid and the elastomeric septum could create a buoyancy that might prevent further sinking of the seal plug into the fluid. However, the trapped air will be vented through a defect in the septum, such as the defect caused by the needle cannula. This venting of air permits further movement of the seal plug into the fluid. Simultaneously, the phases of the fluid will be separating such that the heavier phase component of the fluid will concentrate closer to the closed bottom, and such that the lighter phase component of the fluid will be closer to the open top. The seal plug will move primarily through the lighter phase component and toward the heavier phase component of the fluid.

The centrifuge may be stopped after the seal plug stabilizes between the separate phases of the fluid. Upon termination of the centrifugal load, the liner will resiliently return toward its unexpanded condition and will sealingly engage outer circumferential regions of the seal plug. As a result, the phases of the fluid sample are isolated from one another by the seal plug and may be separated for subsequent analysis.

When the fluid sample is blood, the higher specific gravity portion that contains the cellular components is between the separator and the bottom of the container after centrifugation. The lower specific gravity portion that contains the cell-free serum fraction or plasma is between the top surface of the separator and the top of the container after centrifugation.

Therefore, at the final position of the separator after centrifugation, the separator is able to substantially eliminate the presence of red blood cells in the lower specific gravity portion and the lower specific gravity is substantially free of cellular contamination.

The assembly of the present invention is advantageous over existing separation products that use gel. In particular, the assembly of the present invention will not interfere with analytes as compared to gels that may interfere with analytes. Another attribute of the present invention is that the assembly of the present invention will not interfere with therapeutic drug monitoring analytes.

Most notably, is that the time to separate a fluid sample into separate densities is achieved in substantially less time with the assembly of the present invention as compared to assemblies that use gel.

Another notable advantage of the present invention is that fluid specimens are not subjected to low density gel residuals that are at times available in products that use gel.

A further attribute of the present invention is that there is no interference with instrument probes.

Another attribute of the present invention is that samples for blood banking tests are more acceptable than when a gel separator is used.

Another attribute of the present invention is that only the substantially cell-free serum fraction of a blood sample is exposed to the top surface of the separator, thus providing practitioners with a clean sample.

Additionally, the assembly of the present invention does not require any additional steps or treatment by a medical practitioner whereby a blood or fluid sample is drawn in the standard fashion, using standard sampling equipment.

DETAILED DESCRIPTION

The present invention may be embodied in other specific forms and is not limited to any specific embodiments described in detail, which are merely exemplary. Various other modifications will be apparent to and readily made by those skilled in the art without departing from the scope and spirit of the invention. The scope of the invention will be measured by the appended claims and their equivalents.

The preferred apparatus of the present invention is illustrated in FIGS. 1 to 9, wherein device 10 comprises a tube 12, an elastomeric liner 22, a closure 34, and a seal plug assembly 64.

Device 10 includes rigid plastic tube 12 having an open top 14, a closed bottom 16 and a cylindrical sidewall 18. Sidewall 18 defines a constant inside diameter "a" along a major portion of its length.

Device 10 further includes an elastomeric liner 22 having an open top 24, a closed bottom 26 and a tubular sidewall 28. Side wall 28, in an unbiased condition, defines an inside diameter "c" and an outside diameter "d" along a major portion of the length of liner 22. Outside diameter "d" is less than inside diameter "a" of sidewall 18 on tube 12, and is approximately equal to or slightly less than inside diameter "b" of rim 20. Liner 22 is characterized by an outwardly directed flange 30 adjacent open top 24. Portions of flange 30 immediately adjacent open top 24 are cylindrically generated and define an outside diameter "e". However, portions of flange 30 spaced from open top 24 taper to outside diameter "d" which exists elsewhere on sidewall 28. Diameter "e" of flange 30 is greater than inside diameter "b" of rim 20 on tube 12, and is approximately equal to or slightly less than inside diameter "a" existing at locations on tube 12 between rim 20 and open top 14 thereof. With these relative diametrical dimensions, portions of liner 22 below flange 30 can be slid through rim 20 on tube 12. Additionally, flange 30 can be slid into portions of tube 12 between rim 20 and open top 14. However, flange 30 will interfere with rim 20 and will prevent liner 22 from sliding entirely past rim 20. The length of liner 22 is selected to ensure that closed bottom 26 of liner 22 is spaced slightly from closed bottom 16 of tube 12 when flange 30 of liner 22 engages rim 20 of tube 12.

A liner stopper 48 extends from liner end seat 44 to bottom end 38 of tube closure 34. Liner stopper 48 has a cylindrical outer surface along most of its length with an outside diameter slightly greater than inside diameter "c" of liner 22. However, portions of liner stopper 48 adjacent bottom end 38 are chamfered to a diameter that is less than inside diameter "c" of liner 22. The chamfered bottom end of liner stopper 48 facilitates the inward compression required to urge liner stopper 48 of tube closure 34 into open top end 24 of liner 22. Liner stopper 48 may further include by at least one axially extending vent groove [50] to permit venting of gas from liner 22 during insertion of tube closure 34.

Tube closure 34 is further characterized by a plug recess 52 extending axially into bottom end 38. The entrance to plug recess 52 is defined by a plurality of circumferentially spaced flexible release walls 54 that have inner surfaces 56 generated as part of a single cylinder with a diameter "f". Each flexible release wall 54 may further include a chamfered surface extending from the cylindrically generated surface 56 to the bottom end 38 of tube closure 34. Flexible release walls 54 each also include a radially aligned plug-gripping surface 60 facing into plug recess 52. The top central portion of plug recess 52 is defined by downwardly pointing conical surface 62.

Device 10 further includes a tube closure that can be pierced by a needle cannula and that will reseal itself after removal of the needle cannula. Tube closure 34 includes a top end 36 and a bottom end 38. Top end 36 of tube closure 34 is characterized by a central recess 40 which defines a target area for piercing by a needle cannula. A radially aligned tube end seat 42 is defined between top and bottom ends 36 and 38 and faces toward bottom end 38. Tube end seat 42 defines an outside diameter that exceeds the outside diameter of tube 12. Thus, tube end seat 42 can be sealingly engaged against open top end 14 of tube 12.

A liner end seat 44 is defined on tube closure 34 at a distance below tube end seat 42 to ensure that liner end seat 44 is substantially adjacent open top end 24 of liner 22 when tube end seat 42 is adjacent to open top end 14 of tube 12. Portions of tube stopper 46 adjacent liner end seat 44 define a diameter approximately equal to inside diameter "a" of tube 12. Portions of tube stopper 46 closer to tube end seat 42 define a larger diameter. Consequently, tube stopper 46 is compressed during insertion into tube 14 for achieving a tight sealing engagement.

A liner stopper 48 extends from liner end seat 44 to bottom end 38 of tube closure 34. Liner stopper 48 has a cylindrical outer surface along most of its length with an outside diameter slightly greater than inside diameter "c" of liner 22. However, portions of liner stopper 48 adjacent bottom end 38 are chamfered to a diameter that is less than inside diameter "c" of liner 22. The chamfered bottom end of liner stopper 48 facilitates the inward compression required to urge liner stopper 48 of tube closure 34 into open top end 24 of liner 22. Liner stopper 48 is further characterized by at least one axially extending vent groove 50 to permit venting of gas from liner 22 during insertion of tube closure 34.

Tube closure 34 is further characterized by a plug recess 52 extending axially into bottom end 38. The entrance to plug recess 52 is defined by a plurality of circumferentially spaced flexible release walls 54 that have inner surfaces 56 generated as part of a single cylinder with a diameter "f". Each flexible release wall 54 further includes a chamfered surface 58 extending from the cylindrically generated surface 56 to the bottom end 38 of tube closure 34. Flexible release walls 54 each also include a radially aligned plug-gripping surface 60 facing into plug recess 52. The top central portion of plug recess 52 is defined by downwardly pointing conical surface 62.

Device 10 further includes a seal plug assembly 64 which comprises a generally tubular hard plastic shell 66 and an elastomeric septum 68. The components of seal plug assembly 64 are formed from materials to exhibit a combined density less than the density of the red blood cells, but greater than the density of the serum. Shell 66 includes a top end 70, a bottom end 72 and a central passage 74 extending continuously between the ends. Annular sealing ribs 76 and 78 extend outwardly from shell 66 at locations near bottom end 72. Annular sealing ribs 76 and 78 define diameters approximately equal to inside diameter "c" of liner 22. Shell 66 further includes an outwardly projecting annular septum flange 80 substantially adjacent top end 70 and an annular closure engagement wall 82 between sealing flange 78 and septum flange 80. Closure engagement wall 82 defines an outside diameter that is substantially equal to the inside diameter of plug recess 52 of tube closure 34. A cylindrical wall 84 extends between closure engagement wall 82 and sealing flange 78. Cylindrical wall 84 defines an outside diameter approximately equal to the inside diameter "f" defined by flexible release walls 54 of tube closure 34. Additionally, cylindrical wall 84 defines a length approximately equal to the axial length of cylindrically generated portions 56 of flexible release walls 54.

Elastomeric septum 68 is molded unitarily from a rupturable elastomeric material such as Kraton copolymer, a urethane or PVC. Septum 68 includes a bottom 86, a generally cylindrical side wall 88 extending upwardly from bottom wall 86 and an initially conically convex top wall 90 extending upwardly from cylindrical side wall 88. A shell recess 92 extends centrally into bottom 86 of septum 68. Shell recess 92 includes a small diameter entry having a length substantially equal to the axial distance between septum flange 80 and closure engaging flange 82 on shell 66. Shell recess 92 further includes a large diameter portion that dimensionally conforms to axial and diametric dimensions of septum flange 80 on shell 66.

Device 10 is assembled by slidably inserting liner 22 into shell 12 until flange 30 of liner 22 is seated against annular rim 20 of tube 12. As noted above, outside diameter "d" of cylindrical side wall 28 of liner 22 is less than inside diameter "a" of cylindrical side wall 18 of tube 12. Accordingly, an annular space will exist between liner 22 and tube 12 at locations between annular rim 20 of tube 12 and closed bottom 16 thereof.

Seal plug 64 then may be assembled by mounting elastomeric septum 68 over top 70 of shell 66. More particularly, septum flange 80 is forcibly urged into shell recess 92 in open bottom 86 of septum 68. Small diameter portions of recess 92 will resiliently engage around portions of shell 66 between septum flange 80 and closure engagement flange 82. Seal plug assembly 64 then is urged into plug recess 52 in bottom end 38 of tube closure 34. This will require an initial outward stretching of portions of tube closure 34 adjacent bottom end 38. However, tube closure 34 will resiliently return toward an undeflected condition with flexible release walls 54 engaged around cylindrical wall 84 between closure engagement flange 82 and annular sealing flange 78. Additionally, conical surface 62 in shell recess 52 of tube closure 34 will cause convexly conical top wall 90 of septum 68 to deflect into concave configuration in nested engagement with conical surface 62.

The assembly of closure 34 and seal plug 64 then is inserted into open top end 14 of tube 12. Sufficient insertion causes annular sealing flanges 76 and 78 of shell 66 to sealingly engage in liner 22. Liner end seat 44 will seat substantially adjacent open top 24 of liner 22. Tube stopper 46 will compress into tight sealing engagement with inner circumferential portions of tube 12 between liner 22 and open top 14 of tube 12. Insertion of tube closure 43 into tube 12 will terminate when tube end seat 42 seats against open top 14 of tube 12.

A needle cannula 94 is used to insert a sample of blood into device 10. More particularly, as shown most clearly in FIG. 3, needle cannula 94 is urged centrally into recess 40 at top end 36 of tube closure 34. Continued advancement of needle cannula 94 will cause a rupturing of conical top wall 90 of septum 68. An appropriate volume of blood 96 then is delivered from needle cannula 94 into liner 22. Portions of tube closure 34 adjacent recess 40 will self-seal upon removal of needle cannula 94. However, conical top wall 90 of septum 68 will remain with a defect.

Figure 1:
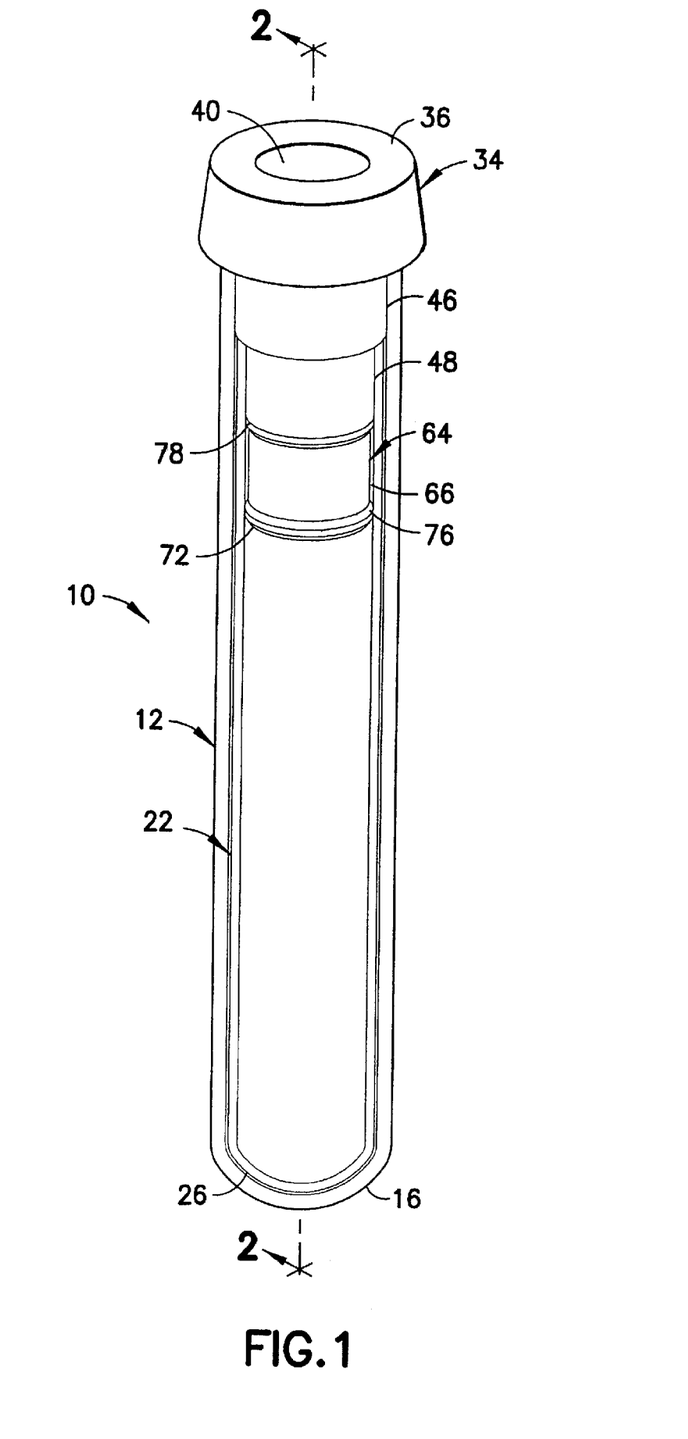
FIG. 1 is a perspective view of a blood collection tube device in accordance with the subject invention.
Figure 2:
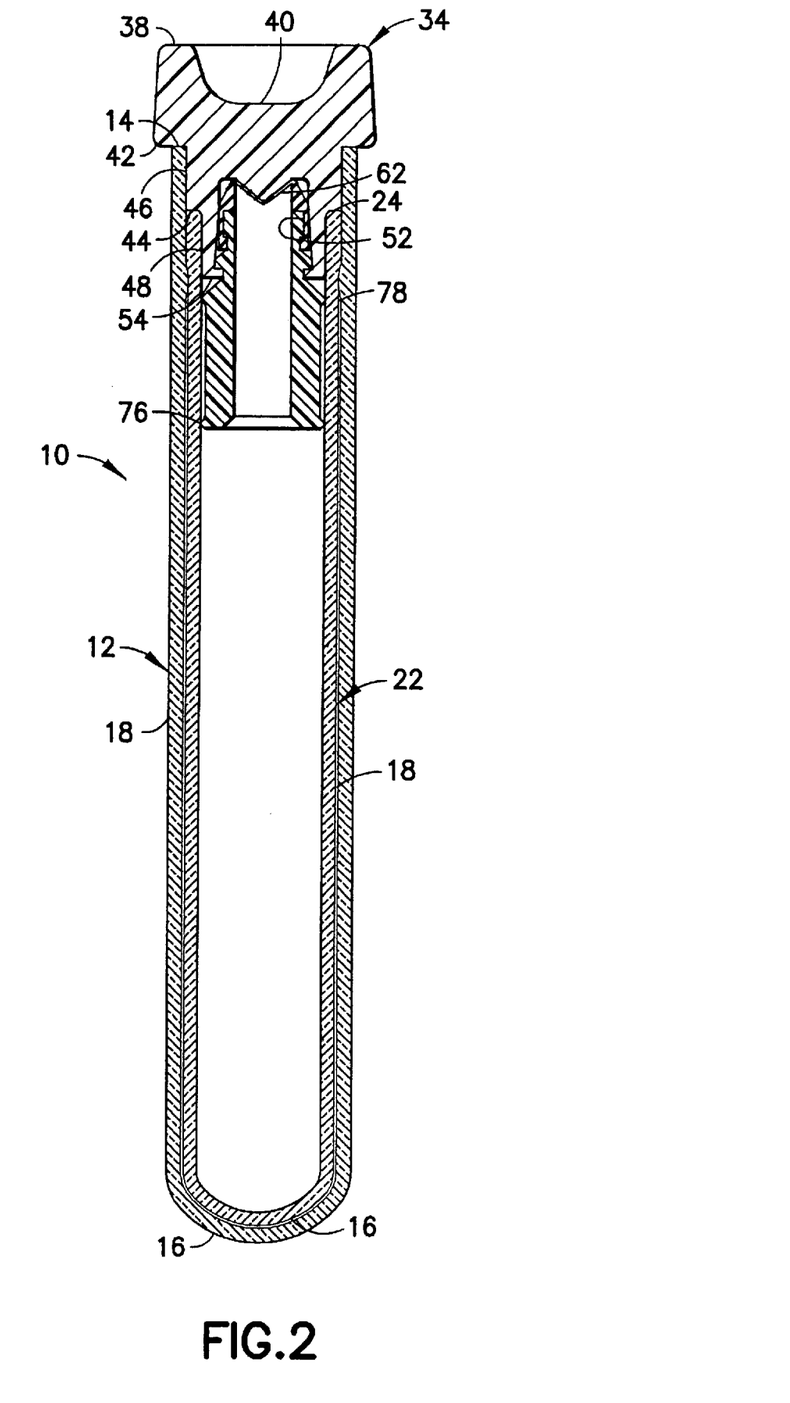
FIG. 2 is a cross-sectional view taken along line 2—2 in FIG. 1.
Figure 3:
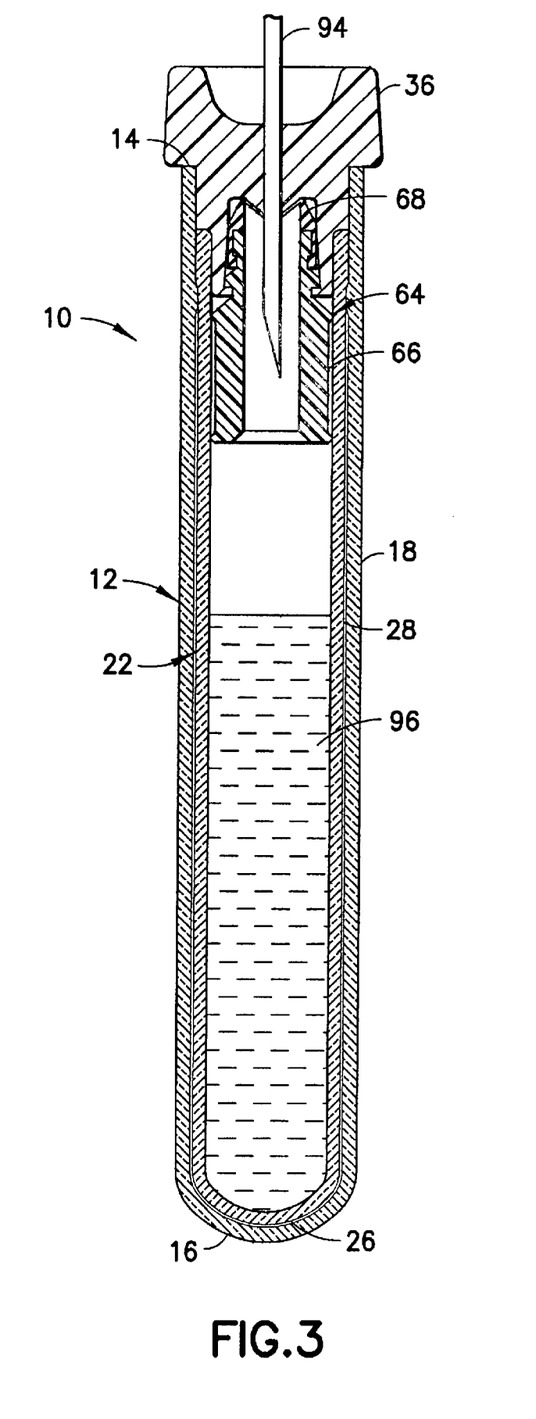
FIG. 3 is a cross-sectional view similar to FIG. 2, but showing the device after insertion of a blood sample therein by a needle cannula.
Figure 4:
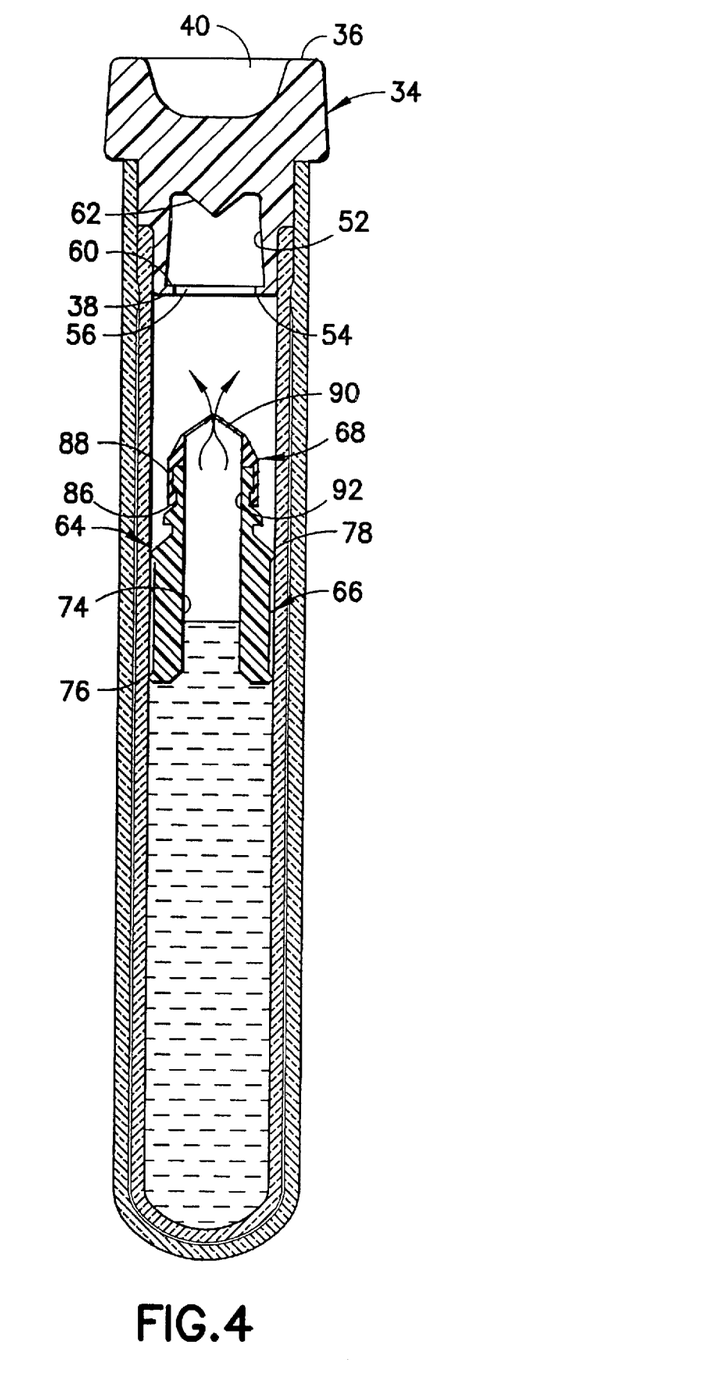
FIG. 4 is a cross-sectional view similar to FIGS. 2 and 3, but showing the device at an early stage during centrifugation.
Figure 5:
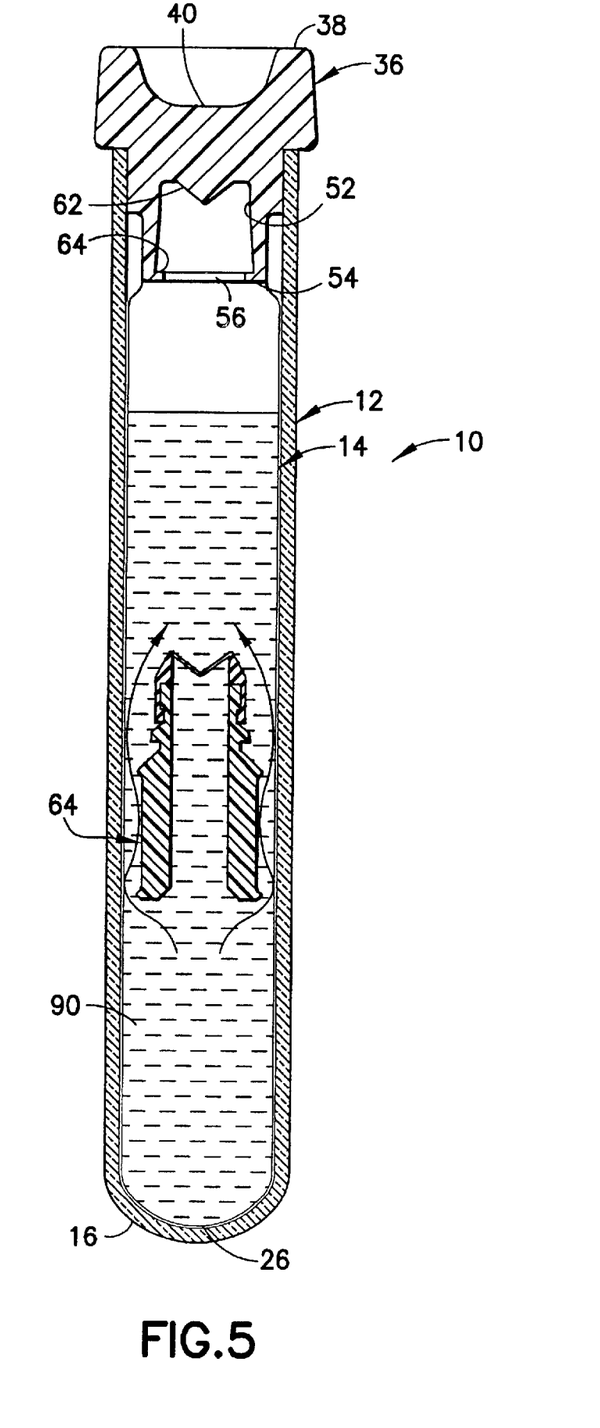
FIG. 5 is a cross-sectional view similar to FIG. 4, but showing the device at a later stage during centrifugation.
Figure 7:
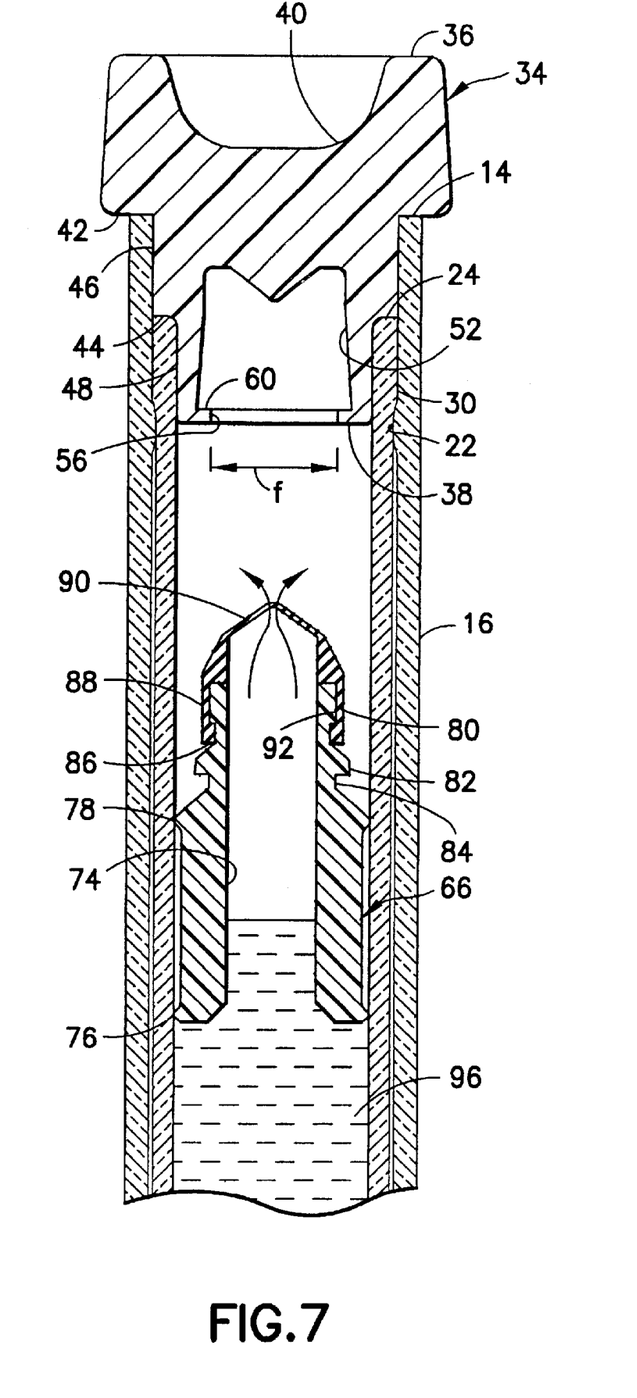
FIG. 7 is an enlarged cross-sectional view of portions of the device adjacent the seal plug during the early stages of centrifugation, as shown in FIG. 4.

Device 10 with blood 96 therein then is placed in a centrifuge which places a centrifugal load on device 10. The centrifugal load deflects flexible release walls 54 sufficiently downwardly to permit separation of seal plug assembly 64 from tube closure 34. Simultaneously, the centrifugal load causes an outward deflection of tubular sidewall 28 of elastomeric tube liner 22. This outward deflection of liner 22 permits seal plug 64 to move toward closed bottoms 26 and 16 of liner 22 and tube 12 respectively. Air will be trapped in passage 74 of shell 66 approximately when bottom end 72 of shell 66 contacts blood 96. This trapped air could restrict further downward movement of seal plug 64. However, the defect in septum 68 caused by needle cannula 94 defines a path through which trapped air may escape passage 74. Thus, seal plug 64 is permitted to sink into blood 96.

The centrifugal load created by the centrifuge also separates serum from red blood cells in blood 96. Thus, red blood cells, under the action of the centrifugal load, migrate around seal plug assembly 64 and toward closed bottom 26 of liner 22. Simultaneously, the less dense serum of blood 96 will flow between shell 66 and outwardly deformed portions of elastomeric liner 22 as shown schematically in FIG. 5.

Figure 6:
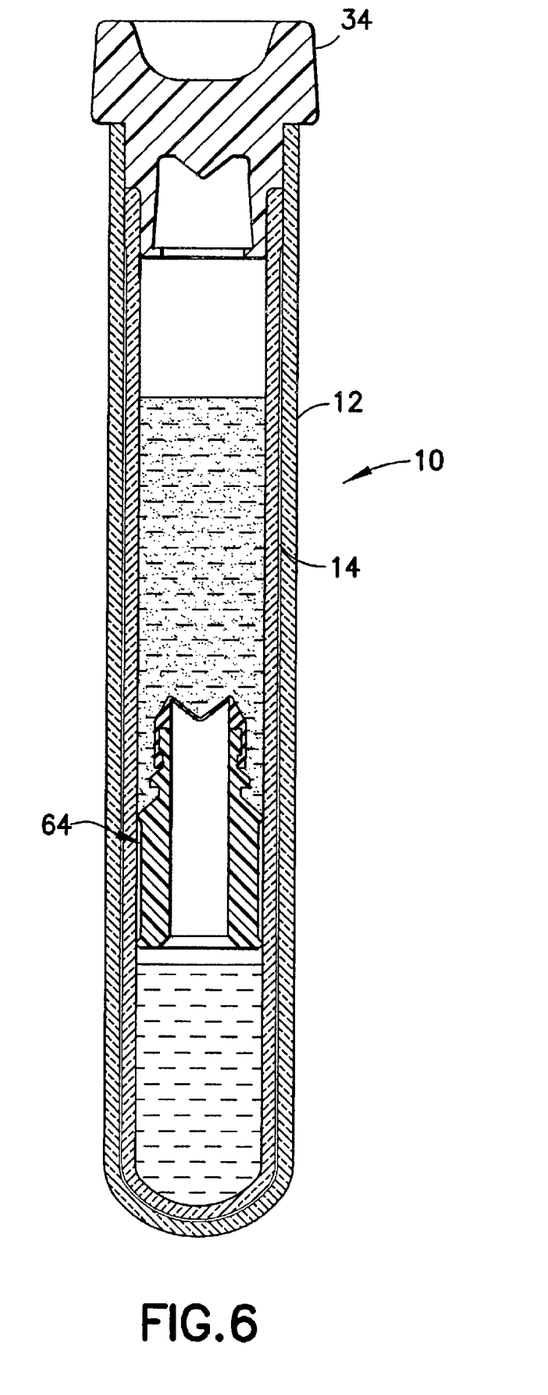
FIG. 6 is a cross-sectional view similar to FIG. 5, but showing the device upon completion of centrifugation, and with the respective phases of blood separated.
Figure 8:
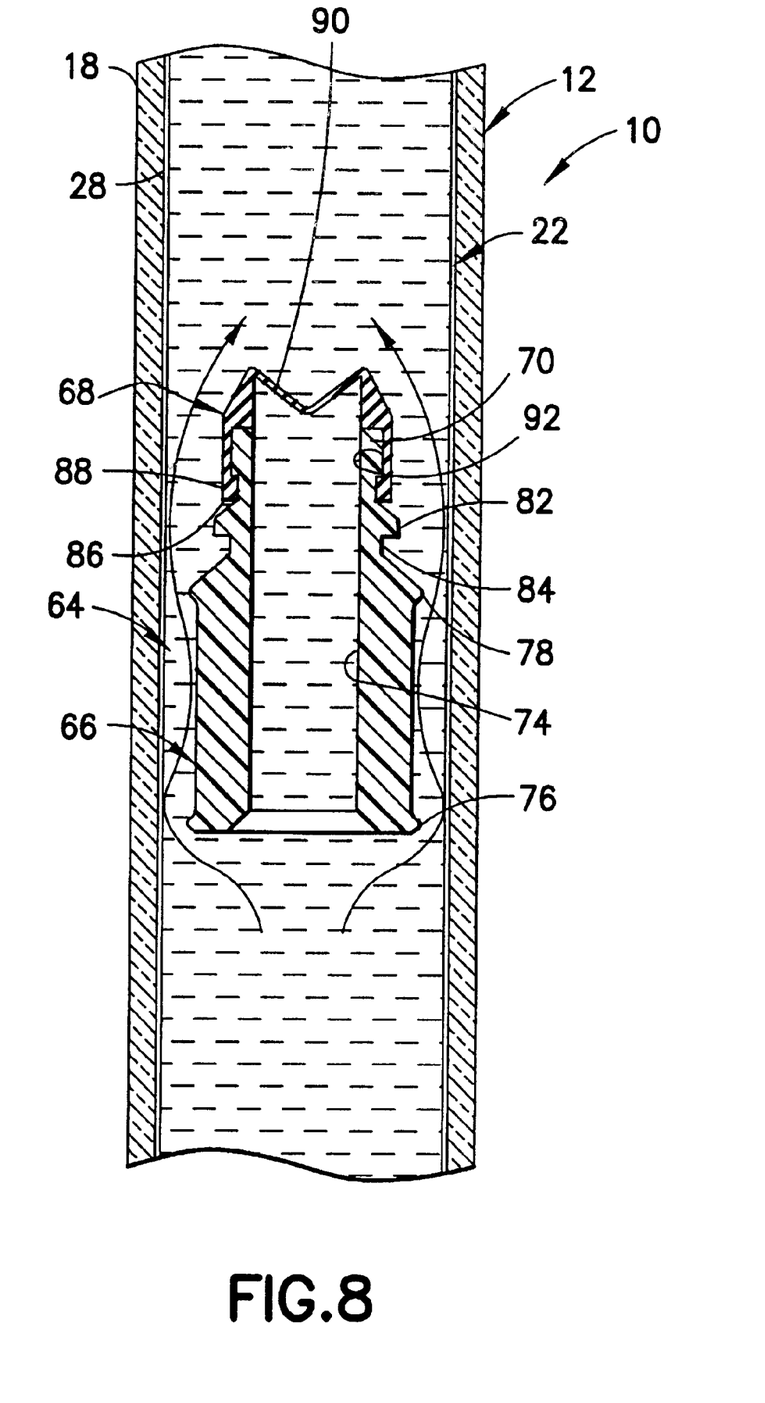
FIG. 8 is an enlarged cross-sectional view of portions of the device adjacent the seal plug at a later stage during centrifugation, as shown in FIG. 5.
Figure 9:
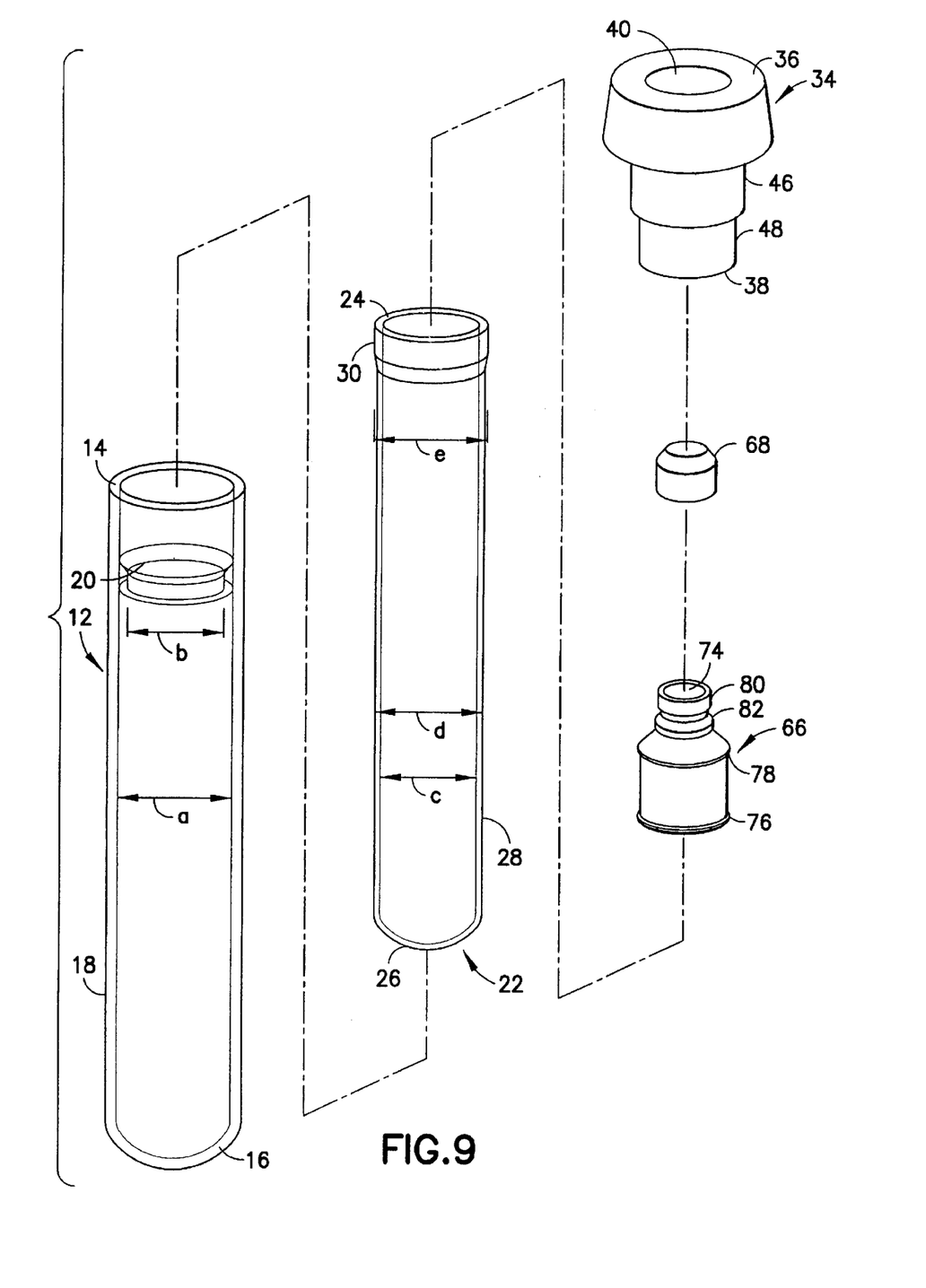
FIG. 9 is an exploded perspective view of the device.

Seal plug 64 will stabilize at a position in liner 22 between the red blood cells and the serum of blood 96. This stabilized position is attributable to the formation of seal plug 66 and septum 68 from materials that will give seal plug 64 a density less than the density of the red blood cells, but greater than the density of the serum. After a specified time, the centrifuge will be stopped. The absence of the centrifugal load will cause side wall 28 of elastomeric liner 22 to resiliently return toward an undeformed condition and into tight sealing engagement with annular sealing flanges 76 and 78 of shell 66. Thus, red blood cells 98 will be sealed between seal plug 64 and closed bottom 26 of liner 22, while serum 100 will lie between seal plug 64 and closure 34.

Liner 22 is compatible with most of the numerous additives used in sample collection tubes such as citrates, silicates, EDTA and the like that are used to condition the fluid sample either to facilitate or retard clotting, or to preserve the fluid sample for a particular analysis. It is within the purview of this invention that one or more additives may be used in the present invention for particular applications.

EXAMPLE 1

The separator of the present invention was made as follows: The three components of the separator, a liner, a septum, a seal plug were made by injection molding. The liner was made from DuPont Dow Engage® 8400 polyolefin elastomer with a flexural modulus of 22 MPa. The septum was made from GLS Dynaflex® 2712 (Dynaflex is a trademark of and manufactured by GLS Corp., Cory, Ill.), with a specific gravity of 0.889. The seal plug was made from Bayer Lustran® 348 ABS with a specific gravity of 1.06.

EXAMPLE 2

The separator of the present invention was made as follows: The two components of the separator, the liner was injection molded from DuPont Dow Engage® 8411 polyolefin elastomer with a flexural modulus of 29 MPa and the seal plug was injection molded from Bayer Lustran ® 348 with a specific gravity of 1.06.

EXAMPLE 3

The separator of the present invention was made as follows: The three components of the separator, the liner was injection molded from DuPont Dow Engage® 8411 polyolefin elastomer with a flexural modulus of 29 MPa and the septum was made from a Kraton® elastomer and the seal plug injection molded from Bayer Lustram® 348 with a specific gravity of 1.06.

What is claimed is:

1. A tube device for separating a blood sample into first and second phases of different respective densities, said device comprising:

a substantially rigid tube having an open top and a closed bottom and an inner circumferential surface;

an elastomeric liner having an open top and a closed bottom and positioned in said tube such that at least portions of said liner are spaced inwardly from said tube, said liner being resiliently expandable such that at least portions of said liner are engageable with said tube in response to loads imposed on said liner;

a tube closure in said open top of said tube; and a seal plug sealingly engaged by said elastomeric liner in an unexpanded condition of said liner, and having a density between the respective densities of the phases of a liquid sample;

whereby when said device is subjected to centrifugal forces, said elastomeric liner deforms causing said seal plug to separate from said liner and moving freely to a position to separate said blood sample into higher and lower density components, and wherein a portion of said tube closure is sealingly engaged in said open top of said liner and urges said open top of said liner into sealing engagement with said inner circumferential surface of said tube.

2. The device of claim 1 wherein the inner circumferential surface of said tube engaged by said liner include an annular inwardly extending rim.

3. The device of claim 2 in the top of said liner includes an outwardly extending flange engageable with said rim of said tube for limiting insertion of said liner into said tube.

4. A tube device for separating a blood sample into first and second phases of different respective densities, said device comprising:

a substantially rigid tube having an open top and a closed bottom and an inner circumferential surface;

an elastomeric liner having an open top and a closed bottom and positioned in said tube such that at least portions of said liner are spaced inwardly from said tube, said liner being resiliently expandable such that at least portions of said liner are engageable with said tube in response to loads imposed on said liner;

a tube closure in said open top of said tube; and a seal plug sealingly engaged by said elastomeric liner in an unexpanded condition of said liner, and having a density between the respective densities of the phases of a liquid sample;

whereby when said device is subjected to centrifugal forces, said elastomeric liner deforms causing said seal plug to separate from said liner and moving freely to a position to separate said blood sample into higher and lower density components, and wherein the tube closure includes a plug recess dimensioned for releasably receiving at least a portion of said seal plug.

5. The device of claim 4 wherein the tube closure includes a plurality of circumferentially spaced flexible release walls for releasably engaging a portion of said seal plug, said flexible release walls being resiliently deflectable toward said closed bottom of said liner in response to a selected load on said device.

6. The device of claim 5 wherein the seal plug includes an annular closure engaging flange disposed in said plug recess of said tube closure and releasably engaged with said flexible release walls of said tube closure.

7. A tube device for separating a blood sample into first and second phases of different respective densities, said device comprising:

a substantially rigid tube having an open top and a closed bottom and an inner circumferential surface;

an elastomeric liner having an open top and a closed bottom and positioned in said tube such that at least portions of said liner are spaced inwardly from said tube, said liner being resiliently expandable such that at least portions of said liner are engageable with said tube in response to loads imposed on said liner;

a tube closure in said open top of said tube; and a seal plug sealingly engaged by said elastomeric liner in an unexpanded condition of said liner, and having a density between the respective densities of the phases of a liquid sample;

whereby when said device is subjected to centrifugal forces, said elastomeric liner deforms causing said seal plug to separate from said liner and moving freely to a position to separate said blood sample into higher and lower density components, and wherein said seal plug includes a substantially rigid generally tubular shell having opposed top and bottom ends and a passage extending therebetween, a rupturable septum sealingly covering portions of said passage adjacent said top end, said septum defining an air vent hole in response to rupturing of said septum by a needle cannula for permitting venting of air through said septum to enable said seal plug to sink into said blood.

8. A tube device for separating a blood sample into first and second phases of different respective densities, said device comprising:

a substantially rigid tube having an open top and a closed bottom and an inner circumferential surface;

an elastomeric liner having an open top and a closed bottom and positioned in said tube such that at least portions of said liner are spaced inwardly from said tube, said liner being resiliently expandable such that at least portions of said liner are engageable with said tube in response to loads imposed on said liner;

a tube closure in said open top of said tube; and a seal plug sealingly engaged by said elastomeric liner in an unexpanded condition of said liner, and having a density between the respective densities of the phases of a liquid sample;

whereby when said device is subjected to centrifugal forces, said elastomeric liner deforms causing said seal plug to separate from said liner and moving freely to a position to separate said blood sample into higher and lower density components, and wherein the seal plug includes a substantially rigid portion having a plurality of annular sealing flanges dimensioned for sealing engagement by said elastomeric liner in an unbiased condition of said liner.

9. A tube device for separating a blood sample into first and second phases of different respective densities, said device comprising:

a substantially rigid tube having an open top and a closed bottom and an inner circumferential surface;

an elastomeric liner having an open top and a closed bottom and positioned in said tube such that at least portions of said liner are spaced inwardly from said tube, said liner being resiliently expandable such that at least portions of said liner are engageable with said tube in response to loads imposed on said liner;

a tube closure in said open top of said tube; and a seal plug sealingly engaged by said elastomeric liner in an unexpanded condition of said liner, and having a density between the respective densities of the phases of a liquid sample;

whereby when said device is subjected to centrifugal forces, said elastomeric liner deforms causing said seal plug to separate from said liner and moving freely to a position to separate said blood sample into higher and lower density components, and wherein said elastomeric liner comprises a non-dimensional stiffness coefficient of about 0.003 to about 190.

* * * * *